United States Patent
Nishitaka et al.

(10) Patent No.: US 12,094,592 B2
(45) Date of Patent: Sep. 17, 2024

(54) ANALYSIS SUPPORT APPARATUS, ANALYSIS SUPPORT SYSTEM, AND ANALYSIS SUPPORT METHOD

(71) Applicant: CANON MEDICAL SYSTEMS CORPORATION, Otawara (JP)

(72) Inventors: Shinya Nishitaka, Nasushiobara (JP); Kazumasa Arakita, Utsunomiya (JP); Masahiro Yoshiwaki, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 339 days.

(21) Appl. No.: 17/453,008

(22) Filed: Nov. 1, 2021

(65) Prior Publication Data
US 2022/0139528 A1    May 5, 2022

(30) Foreign Application Priority Data

Nov. 4, 2020   (JP) ................................. 2020-184638

(51) Int. Cl.
*G16H 30/20* (2018.01)
*G06T 7/00* (2017.01)
*G16H 30/40* (2018.01)

(52) U.S. Cl.
CPC ........... *G16H 30/20* (2018.01); *G06T 7/0012* (2013.01); *G16H 30/40* (2018.01); *G06T 2207/10081* (2013.01)

(58) Field of Classification Search
CPC ... A61B 8/5223; A61B 6/5205; G06T 7/0012; G06T 2207/30004; G06T 2207/10081;
(Continued)

(56) References Cited

U.S. PATENT DOCUMENTS 6,270,457 B1 *  8/2001  Bardy .................... A61B 5/686
                                                          128/920
7,379,885 B1 *  5/2008  Zakim ..................... G16H 20/10
                                                          600/300
(Continued)

FOREIGN PATENT DOCUMENTS

JP          06-251038 A      9/1994
JP       2003-270543 A      9/2003
(Continued)

OTHER PUBLICATIONS

McGhee, Timothy L., et al. "Vital signs reassessment frequency recommendation." Nursing Management 47.9 (2016): 11-12. (Year: 2016).*

(Continued)

*Primary Examiner* — Aaron W Carter
*Assistant Examiner* — Courtney Joan Nelson
(74) *Attorney, Agent, or Firm* — Oblon, McClelland, Maier & Neustadt, L.L.P.

(57) ABSTRACT

An analysis support apparatus according to an embodiment includes processing circuitry. The processing circuitry acquires a medical image that a patient is imaged. The processing circuitry specifies non-image information related to the medical image out of a plurality of pieces of non-image information regarding the patient. The processing circuitry outputs an analysis result of the medical image using the specified non-image information.

14 Claims, 5 Drawing Sheets

(58) Field of Classification Search
CPC .. G06T 2211/424; G16H 10/60; G16H 50/30; G16H 50/20; G16H 15/00; G16H 30/20; G16H 30/40
See application file for complete search history.

(56) References Cited

U.S. PATENT DOCUMENTS

| | | | |
|---|---|---|---|
| 7,815,568 B2* | 10/2010 | Linberg | G16H 40/67 |
| | | | 600/300 |
| 8,355,925 B2* | 1/2013 | Rothman | G16H 50/20 |
| | | | 705/2 |
| 2009/0136111 A1* | 5/2009 | Jabri | G16H 15/00 |
| | | | 382/132 |

FOREIGN PATENT DOCUMENTS

| | | |
|---|---|---|
| JP | 2004-290428 A | 10/2004 |
| JP | 2009-011829 A | 1/2009 |
| JP | 2011-505949 A | 3/2011 |

OTHER PUBLICATIONS

Japanese Office Action dated May 7, 2024, issued in Japanese Patent Application No. 2020-184638.

\* cited by examiner

FIG.1

FIG.3

ANALYSIS SUPPORT APPARATUS, ANALYSIS SUPPORT SYSTEM, AND ANALYSIS SUPPORT METHOD

CROSS-REFERENCE TO RELATED APPLICATIONS

This application is based upon and claims the benefit of priority from Japanese Patent Application No. 2020-184638, filed on Nov. 4, 2020; the entire contents of which are incorporated herein by reference.

FIELD

Embodiments described herein relate generally to an analysis support apparatus, an analysis support system, and an analysis support method.

BACKGROUND

There is a conventionally known technique for allowing a doctor to analyze a medical image by use of an analysis application. In such an analysis application, non-image information regarding a patient is sometimes used in addition to the medical image as an analysis object. With regard to such a technique, manually collecting and inputting various types of non-image information into the analysis application may increase the workload of the doctor.

DETAILED DESCRIPTION

Hereinafter, embodiments of an analysis support apparatus, an analysis support system, and an analysis support method will be described in detail with reference to the drawings.

First Embodiment

An analysis support apparatus according to an embodiment includes processing circuitry. The processing circuitry acquires a medical image that a patient is imaged. The processing circuitry specifies non-image information related to the medical image out of a plurality of pieces of non-image information regarding the patient. The processing circuitry outputs an analysis result of the medical image using the specified non-image information.

Figure 1:
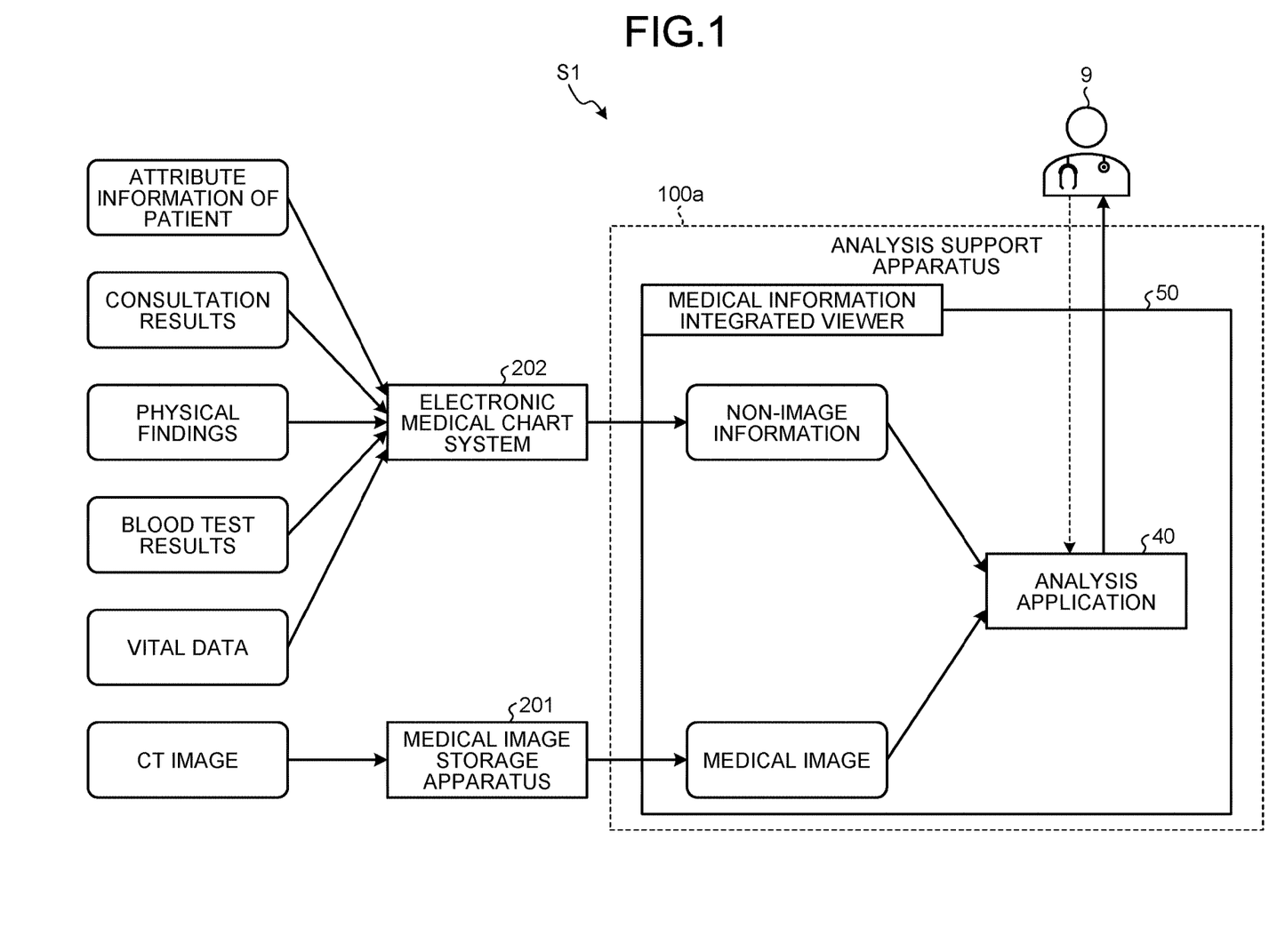
FIG. 1 is a diagram illustrating a configuration example of an analysis support system according to a first embodiment.

FIG. 1 is a diagram illustrating a configuration example of an analysis support system S1 according to a first embodiment. As illustrated in FIG. 1, the analysis support system S1 includes an analysis support apparatus 100a. In the present embodiment, the analysis support system S1 does not include a medical image storage apparatus 201 and an electronic medical chart system 202. The analysis support system S1 may also include the medical image storage apparatus 201 and the electronic medical chart system 202.

The medical image storage apparatus 201 is implemented by, for example, a picture archiving and communication system (PACS), and stores medical images regarding patients in a format based on digital imaging and communications in medicine (DICOM). The medical image regarding a patient is an image obtained by imaging the patient by a medical image diagnostic apparatus. Any type of medical image diagnostic apparatus may be used. In the present embodiment, a case in which the medical image is a computed tomography (CT) image captured by an X-ray CT apparatus will be described as an example, whereas the medical image is not limited to this example. For instance, the medical image may be a magnetic resonance image, an ultrasonic image, or an X-ray image.

The electronic medical chart system 202 stores electronic medical chart data including information regarding patients in a memory within the system. Examples of the information regarding a patient stored in the electronic medical chart system 202 include attribute information of the patient, doctor's consultation results for the patient, doctor's physical findings for the patient, blood test results of the patient, and vital data. Note that they are merely examples, and the electronic medical chart system 202 may store other information. For instance, the electronic medical chart system 202 may further store a medical history of the patient and a consultation history at a medical institution.

Examples of the attribute information of the patient include the age, gender, height, and weight of the patient, whereas the attribute information is not limited to these examples.

The consultation results are information obtained by a doctor asking the patient about his/her condition. For instance, the consultation results include information about subjective symptoms of the patient.

The physical findings are information obtained by a doctor conducting inspection, auscultation, palpation, percussion, tendon reflex, pupillary light reflex or the like of the patient. Examples of the physical findings include information about the presence/absence of paralysis of the body of the patient, and a body part where the paralysis occurs.

The physical findings and the consultation results are inputted by, for instance, an emergency physician who treats the patient taken to hospital in emergency, or an attending physician of the patient.

The analysis support apparatus 100a is an information processing apparatus capable of executing an analysis application 40 for analyzing the medical image regarding the patient. For example, the analysis application 40 specifies a lesion part by image analysis out of the body tissues of the patient visualized in the medical image. Note that the analyzing function contents of the analysis application 40 are not limited to this example. For instance, the analysis application 40 has a known computer aided diagnosis/detection (CAD) function.

In the example illustrated in FIG. 1, the analysis application 40 is executed as one function of a medical information integrated viewer 50 that displays information of treatments or examinations on the patient. The medical information integrated viewer 50 is a viewer capable of displaying various types of medical information regarding the patient. The medical information integrated viewer 50 may also have a function as a graphical user interface (GUI) that receives data input or the like from a user 9. The analysis application 40 may also be executed as a different function from the medical information integrated viewer 50.

The analysis support apparatus 100a acquires the medical image as an analysis object from the medical image storage apparatus 201.

In the present embodiment, information regarding the patient other than the medical image is referred to as "non-image information". Some of various types of non-image information stored in the electronic medical chart system 202 are used for analyzing the medical image by the analysis application 40.

The analysis support apparatus 100a collects the non-image information used for analyzing the medical image from the electronic medical chart system 202. For example, a parameter for inputting prescribed non-image information is provided in the analysis application 40. Different pieces of non-image information may be used for analyzing the medical image by the analysis application 40 depending on a part as an imaging object of the medical image or the like.

Additionally, when new non-image information is stored in the electronic medical chart system 202 or the contents of the collected non-image information are changed, the analysis support apparatus 100a recollects the new non-image information or the changed non-image information during a prescribed period after initially collecting the non-image information. The recollection of the non-image information will be described in detail later.

The medical image storage apparatus 201 and the electronic medical chart system 202 are examples of a medical information processing apparatus in the present embodiment. The analysis support apparatus 100a may acquire the medical image from the electronic medical chart system 202 when the medical image is registered in the electronic medical chart system 202.

The analysis support apparatus 100a may also acquire the medical image or the non-image information from a medical information processing apparatus other than the medical image storage apparatus 201 and the electronic medical chart system 202.

The user 9 of the analysis application 40 is, for example, a doctor such as a diagnostic reading doctor. The user 9 refers to a result analyzed by the analysis application 40, thereby grasping, for instance, the location of the lesion part of the patient. In the present embodiment, the user 9 of the analysis application 40 is described as a different person from the doctor who inputs the physical findings or the consultation results, whereas the user 9 and the doctor may be the same person.

Next, the analysis support apparatus 100a of the present embodiment will be described in detail.

Figure 2:
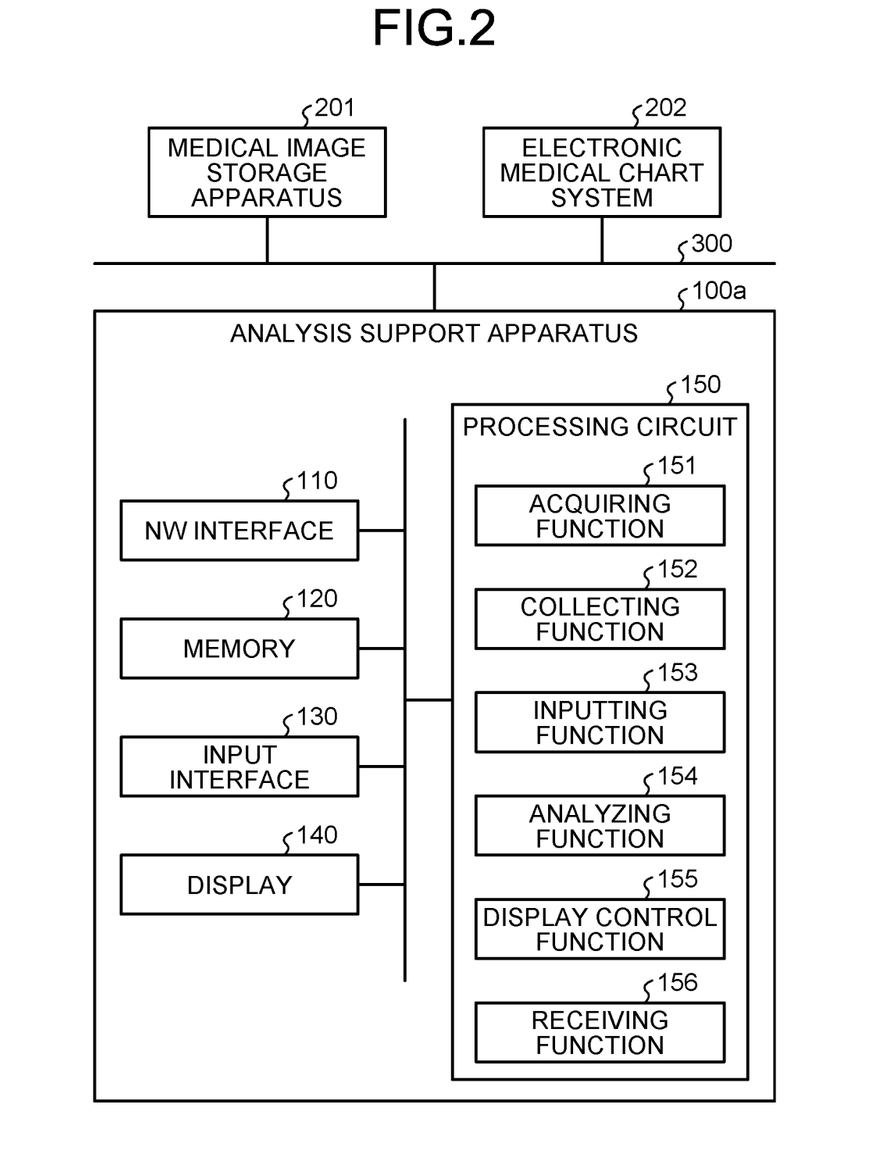
FIG. 2 is a diagram illustrating a configuration example of an analysis support apparatus according to the first embodiment.

FIG. 2 is a diagram illustrating a configuration example of the analysis support apparatus 100a according to the first embodiment. As illustrated in FIG. 2, the analysis support apparatus 100a includes a network (NW) interface 110, a memory 120, an input interface 130, a display 140, and a processing circuit 150. The analysis support apparatus 100a is connected to the medical image storage apparatus 201 and the electronic medical chart system 202 via a network 300 such as an in-hospital local area network (LAN) so as to allow communication therebetween.

The NW interface 110 is connected to the processing circuit 150. The NW interface 110 controls transmission of various data between the analysis support apparatus 100a and the medical image storage apparatus 201 or the electronic medical chart system 202, and communication therebetween. The NW interface 110 is implemented by, for instance, a network card, a network adapter, or a network interface controller (NIC).

The memory 120 stores various types of information used in the processing circuit 150 in advance. The memory 120 also stores various computer programs. The memory 120 may be provided outside the analysis support apparatus 100a.

The input interface 130 is implemented by, for instance, a trackball, a switch button, a mouse, a keyboard, a touchpad that allows a user to perform an input operation by touching an operation surface, a touchscreen obtained by integrating a display screen and a touchpad, a noncontact input circuit using an optical sensor, or a voice input circuit. The input interface 130 is connected to the processing circuit 150 to convert input operations received from an operator to electric signals and output the electric signals to the processing circuit 150. In the present specification, the input interface 130 is not limited to those including a physical operation component such as a mouse and a keyboard. Examples of the input interface 130 also include an electric signal processing circuit that receives an electric signal corresponding to an input operation from external input equipment provided separately from the apparatus, and outputs the electric signal to the processing circuit 150.

The display 140 is, for instance, a liquid crystal display or an organic electro-luminescence (OEL) display. The input interface 130 and the display 140 may be integrated. For example, the input interface 130 and the display 140 may be implemented by a touch panel. The display 140 is an example of a display unit in the present embodiment. The display 140 may be provided outside the analysis support apparatus 100a.

The processing circuit 150 is a processor that reads from the memory 120 and executes the computer programs, thereby implementing functions corresponding to the respective computer programs. The processing circuit 150 of the present embodiment includes an acquiring function 151, a collecting function 152, an inputting function 153, an analyzing function 154, a display control function 155, and a receiving function 156. The acquiring function 151 is an example of an acquiring unit. The collecting function 152 is an example of a collecting unit or a specifying unit. The inputting function 153 is an example of an inputting unit. The analyzing function 154 is an example of an analyzing unit. Additionally, the analyzing function 154 is a function equivalent to the analysis application 40 described using FIG. 1. Note that illustration of other functions of the medical information integrated viewer 50 is omitted in FIG. 2. The display control function 155 is an example of a display control unit or a notifying unit. The receiving function 156 is an example of a receiving unit.

For instance, the respective processing functions including the acquiring function 151, the collecting function 152, the inputting function 153, the analyzing function 154, the display control function 155, and the receiving function 156, as constituent elements of the processing circuit 150, are stored in the memory 120 in the forms of computer programs executable by a computer. The processing circuit 150 is a processor. For example, the processing circuit 150 reads from the memory 120 and executes the computer programs, thereby implementing the functions corresponding to the respective computer programs. In other words, the processing circuit 150 has the respective functions illustrated in the processing circuit 150 in FIG. 2 in a state in which the processing circuit 150 reads the corresponding computer programs. While FIG. 2 illustrates the example in which the single processor implements the processing functions performed by the acquiring function 151, the collecting function 152, the inputting function 153, the analyzing function 154, the display control function 155, and the receiving function 156, the processing circuit 150 may be configured by combining a plurality of independent processors together to implement the functions with the respective processors executing the computer programs. Additionally, while FIG. 2 illustrates the example in which the single memory 120 stores the computer programs corresponding to the respective processing functions, the computer programs may be dispersedly stored in a plurality of memory, and the processing circuit 150 may read the individual computer programs from the corresponding memory.

While the example in which the "processor" reads from the memory and executes the computer programs corresponding to the respective functions has been described above, the embodiments are not limited to this example. For instance, the term "processor" indicates a central processing unit (CPU), a graphics processing unit (GPU), or a circuit such as an application specific integrated circuit (ASIC) and a programmable logic device (e.g., a simple programmable logic device (SPLD), a complex programmable logic device (CPLD), and a field programmable gate array (FPGA)). For example, when the processor is a CPU, the processor reads and executes the computer programs stored in the memory 120 to implement the functions. Meanwhile, when the processor is an ASIC, the functions are directly incorporated in the circuit of the processor as a logic circuit instead of storing the computer programs in the memory 120. The respective processors in the present embodiment are not limited to single-circuit processors. A plurality of independent circuits may be combined and integrated as one processor to implement the functions. Moreover, a plurality of constituent elements in FIG. 2 may be integrated as one processor to implement the functions.

The acquiring function 151 acquires a medical image where a patient is imaged. For example, the acquiring function 151 acquires the medical image as an analysis object from the medical image storage apparatus 201 via the network 300 and the NW interface 110. For instance, the medical image as the analysis object may be selected by the user 9, or retrieved using identification information or the like of the patient as a diagnosis object.

The collecting function 152 specifies non-image information related to the medical image out of a plurality of pieces of non-image information regarding the patient, and collects the specified non-image information. For example, the non-image information related to the medical image is non-image information required to analyze the medical image. More specifically, the collecting function 152 collects the non-image information regarding the patient, used for analyzing the medical image by the analyzing function 154, which will be described later, from one or a plurality of medical information processing apparatuses. In the present embodiment, the collecting function 152 collects the non-image information used for analyzing the medical image by the analyzing function 154 from the electronic medical chart system 202 via the network 300 and the NW interface 110. While the function of specifying the non-image information required to analyze the medical image and the function of collecting the specified non-image information are described as one function in the present embodiment, the specifying function and the collecting function may be configured as separate functions.

The non-image information used for analyzing the medical image by the analyzing function 154 is set in advance. The collecting function 152 collects information corresponding to the non-image information previously set to be used for analyzing the medical image by the analyzing function 154 out of a plurality of pieces of information stored in the electronic medical chart system 202.

For example, suppose that the "age", "gender", "presence/absence of paralysis", and "part where paralysis occurs" of the patient as the analysis object are set in advance as the non-image information used for analyzing the medical image by the analyzing function 154. In this case, the collecting function 152 retrieves these pieces of non-image information from the electronic medical chart system 202. The collecting function 152 collects the information stored in the electronic medical chart system 202 out of pieces of non-image information. Note that the items of the non-image information as a collection object described above are merely examples, and the collection object is not limited to these examples.

The collecting function 152 transmits the collected non-image information to the inputting function 153.

In some cases, information input into the electronic medical chart system 202 by a doctor has not been completed at the time of initial analysis. For example, suppose that the "presence/absence of paralysis" and the "part where paralysis occurs" out of the non-image information as the collection object have not been registered yet when the collecting function 152 initially searches the electronic medical chart system 202. In this case, the collecting function 152 transmits the "age" and the "gender" that have already been stored in the electronic medical chart system 202 out of the non-image information as the collection object to the inputting function 153 as an initial collection result.

The collecting function 152 also determines whether new non-image information is stored in the electronic medical chart system 202 during a prescribed period after the initial collection. For example, the collecting function 152 repeatedly retrieves the non-image information used for analyzing the medical image by the analyzing function 154 from the electronic medical chart system 202 during the prescribed period after the initial collection, and determines that the new non-image information is stored when the retrieval result includes the non-image information that had not been registered at the time of the previous retrieval. The collection object of the collecting function 152 is the non-image information used for analyzing the medical image by the analyzing function 154. Thus, even when information not used for analyzing the medical image is newly registered in the electronic medical chart system 202, the collecting function 152 does not collect this information.

When the new non-image information as the collection object is stored in the electronic medical chart system 202, the collecting function 152 collects this non-image information as the collection object. For example, when the "presence/absence of paralysis" and the "part where paralysis occurs" that had not been registered at the time of the initial collection are added to the electronic medical chart system 202, the collecting function 152 collects the "presence/absence of paralysis" and the "part where paralysis occurs", and transmits these pieces of collected non-image information to the inputting function 153.

The prescribed period may have any length. For example, the number of days may be set in advance. The prescribed period may also be terminated by a prescribed medical event. Examples of the prescribed medical event include making of a definite diagnosis of the patient as the analysis object, determination of National Health Insurance (NHI) points (medical service fees) of the patient as the analysis object, and completion of a post-diagnostic follow-up period of the patient as the analysis object. The collecting function 152 may acquire information indicating whether the NHI points (medical service fees) are determined from an unillustrated hospital accounting system.

The user 9 may also be able to change the length of the prescribed period. For example, when the user 9 finishes reading the medical image, or judges that it is unnecessary to additionally collect the non-image information anymore, the user 9 may perform an operation of terminating the prescribed period. Alternatively, the user 9 may perform an operation of extending the length of the prescribed period from the preset length.

Moreover, the collecting function 152 may determine whether the non-image information is updated in or added to the electronic medical chart system 202 at any frequency during the prescribed period. For example, a determination timing at which the collecting function 152 determines whether the non-image information is updated in or added to the electronic medical chart system 202 may be set to a prescribed time interval of several minutes or several tens of minutes. Note that the prescribed time interval is not limited to this example.

Additionally, the determination frequency may be changed. For instance, the collecting function 152 may change the determination frequency when a prescribed medical event occurs. More specifically, when the prescribed period includes the post-diagnostic follow-up period, the collecting function 152 may change the prescribed time interval such that the determination frequency is reduced after such a medical event as to make a diagnosis as compared to before the medical event. A time interval between a certain determination timing and a subsequent determination timing does not have to be constant.

The collecting function 152 determines whether the collected non-image information is changed in the electronic medical chart system 202 during the prescribed period after the initial collection. When the non-image information is changed and the changed non-image information satisfies a prescribed condition, the collecting function 152 collects the changed non-image information.

The prescribed condition is, for instance, a threshold for the magnitude of a difference in the non-image information before and after the change. When the difference in the non-image information before and after the change is equal to or larger than the threshold, the collecting function 152 collects the changed non-image information. The threshold may be previously set for each item of the non-image information. For example, the prescribed condition for determining whether to recollect the "age" out of the non-image information is that the magnitude of a difference in the age before and after a change is 5 years or more. That is, the threshold for the magnitude of the difference in the "age" before and after the change is "5". This is because some items do not influence an analysis result of the medical image a lot when changed a little.

The prescribed condition may be set in advance or set by the user 9.

The prescribed condition may be employed only when the non-image information is changed, or may also be employed when the non-image information is newly added, not updated. For example, when the non-image information set as the collection object, but having importance smaller than the threshold, is newly added, the collecting function 152 does not have to collect this non-image information. Alternatively, every time the non-image information set as the collection object is newly added, the collecting function 152 may collect this non-image information.

The inputting function 153 inputs the non-image information collected by the collecting function 152 to the analyzing function 154. For example, the inputting function 153 inputs the corresponding non-image information to each of a plurality of parameters provided in the analyzing function 154. In the present embodiment, the collecting function 152 and the inputting function 153 are separated, whereas the collecting function 152 and the inputting function 153 may be integrated as one function.

The analyzing function 154 analyzes the medical image regarding the patient. More specifically, the analyzing function 154 outputs the analysis result of the medical image using the non-image information specified by the collecting function 152. The analysis result of the medical image using the non-image information may be obtained by using the non-image information during an analysis process of the medical image, or by applying processing or filtering based on the non-image information to a result of analyzing the medical image without using the non-image information. In the present embodiment, the analyzing function 154 analyzes the medical image based on the non-image information collected by the collecting function 152. That is, in the present embodiment, the analysis result of the medical image using the non-image information means the one obtained by using the non-image information during the analysis process of the medical image. Additionally, a known method can be applied as the analysis method.

When the collecting function 152 collects the new non-image information after the analysis of the medical image, the analyzing function 154 reanalyzes the medical image based on the new non-image information.

When the collecting function 152 collects the changed non-image information after the analysis of the medical image, the analyzing function 154 reanalyzes the medical image based on the changed non-image information.

For instance, a case in which the medical image is a CT image of the head of the patient will be described as an example. Suppose that the "presence/absence of paralysis" and the "part where paralysis occurs" out of the non-image information as the collection object have not been collected at the time of the initial analysis. For example, when the patient is taken to hospital in emergency, the CT image may be captured before inputting the physical findings into the electronic medical chart system 202.

In this case, the analyzing function 154 analyzes the medical image without using the "presence/absence of paralysis" and the "part where paralysis occurs" in the initial analysis. Since a paralysis state of the body cannot be read from the CT image, the analyzing function 154 analyzes a lesion part by evenly analyzing both of the left brain and the right brain of the patient at this time. The analyzing function 154 generates, for instance, an image displaying a region that is possibly the lesion part within the entire brain as the analysis result.

When the collecting function 152 newly collects the "presence/absence of paralysis" and the "part where paralysis occurs" after the initial analysis, the analyzing function 154 reanalyzes the CT image by using the "presence/absence of paralysis" and the "part where paralysis occurs". For example, when the patient has paralysis and the part where the paralysis occurs is the right half of the body, the analyzing function 154 analyzes the left brain rather than the right brain with high accuracy. Performing such focused analysis on a specific part based on the non-image information enables the analyzing function 154 to use an appropriate analysis algorithm. Thus, the analyzing function 154 can improve the accuracy of the analysis result in the reanalysis as compared to the previous analysis. The analyzing function 154 updates the analysis result by such reanalysis. The analyzing function 154 may also generate an image in which only the left brain is displayed or an image in which the left brain is highlighted as the analysis result. The analyzing function 154 can perform analysis by limiting a display object as described above.

The analyzing function 154 transmits the analysis result to the display control function 155.

The display control function 155 causes the display 140 to display the analysis result obtained by the analyzing function 154.

Additionally, when the analyzing function 154 reanalyzes the medical image and the analysis result differs before and after the reanalysis, the display control function 155 notifies the user 9 that the analysis result of the medical image is updated. The case in which "the analysis result differs" may be determined based on any criterion. When the degree of difference is equal to or smaller than the criterion, the user 9 does not have to be notified. The criterion may be set in advance, or may be set by the user 9. By limiting the notification to the user 9 to the case in which the analysis result differs before and after the reanalysis, the display control function 155 reduces an increase in checking workload of the user 9 due to being notified more than is necessary.

Figure 3:
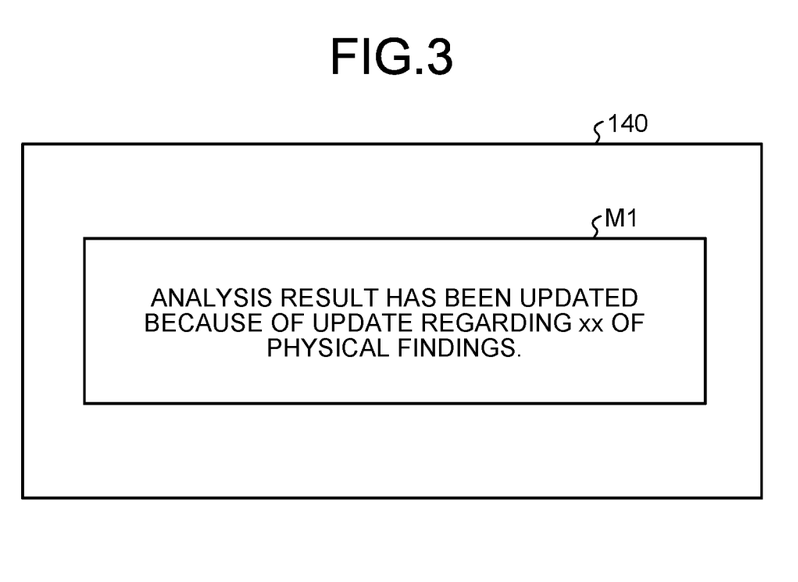
FIG. 3 is a view illustrating an example of a notification screen according to the first embodiment.

FIG. 3 is a view illustrating an example of a notification screen according to the first embodiment. As illustrated in FIG. 3, the display control function 155 causes the display 140 to display a message Ml indicating an explanation of the updated or added non-image information and that the analysis result of the medical image has been updated because of the update or addition of the non-image information. For example, when the user 9 performs an operation of pushing the message Ml, the display control function 155 causes the display 140 to display the updated analysis result.

In the example illustrated in FIG. 3, the message Ml says "The analysis result has been updated because of update regarding xx of the physical findings.", whereas the message Ml is not limited to this example. For instance, the message Ml may include a sentence for encouraging the user 9 to check the analysis result. Additionally, the message Ml does not necessarily have to be displayed, and the analysis result may be automatically displayed in the display 140.

Note that the notification method is not limited to the message notification, and notification using voice or the like may be employed. While the display control function 155 is an example of the notifying unit in the present embodiment, a voice output control function or the like may be provided as the notifying unit.

Returning to FIG. 2, the receiving function 156 receives various operations from the user 9. For example, the receiving function 156 receives an operation of instructing the start of an image analysis process from the user 9. The receiving function 156 receives an operation of terminating the prescribed period from the user 9. The receiving function 156 receives an operation of extending the length of the prescribed period from the user 9. The receiving function 156 receives an operation of pushing the message Ml from the user 9. The receiving function 156 transmits the contents of the received operations to the acquiring function 151, the collecting function 152, or the display control function 155.

Next, a flow of the image analysis process according to the present embodiment having the configuration as described above will be described.

Figure 4:
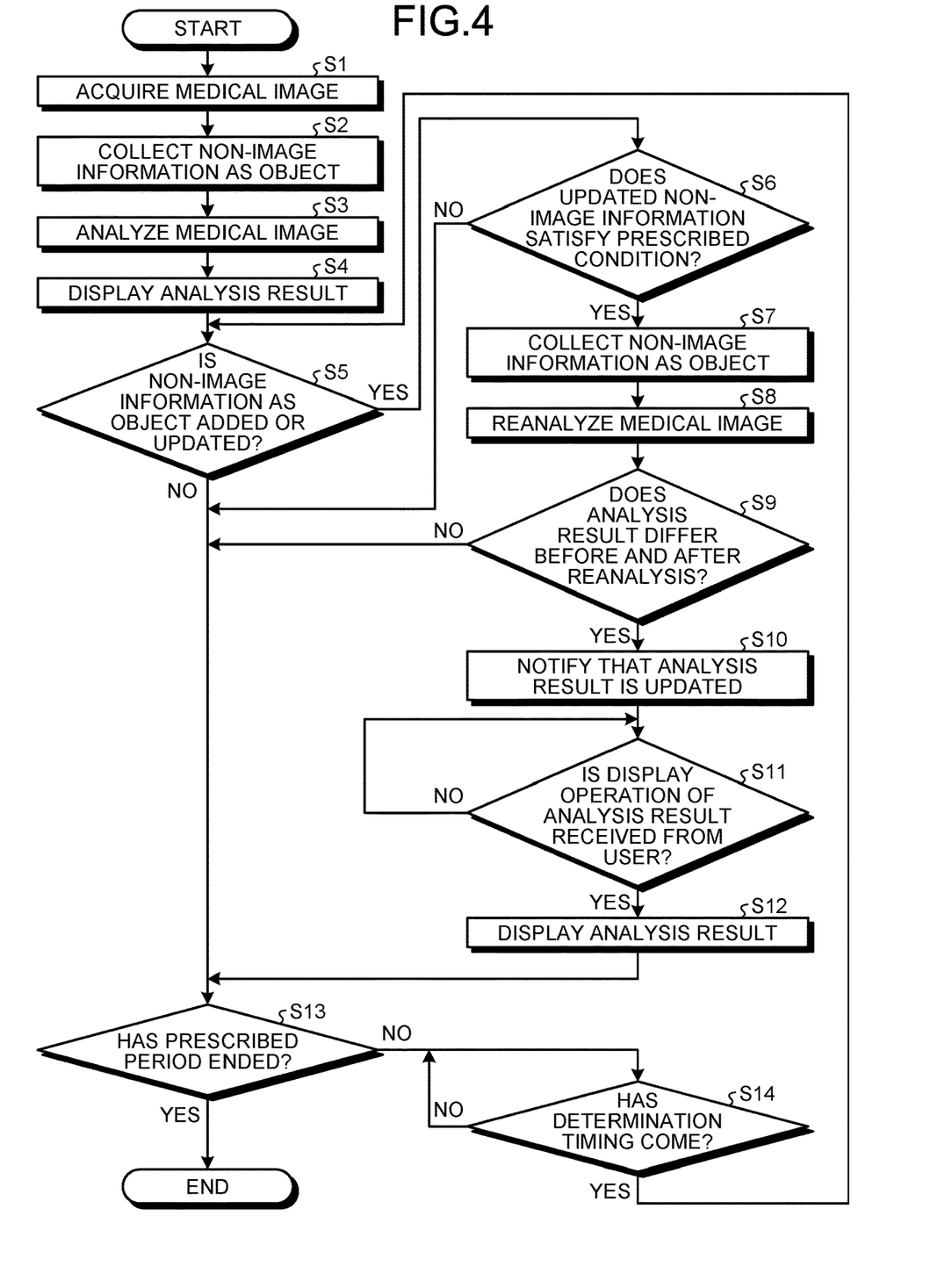
FIG. 4 is a flowchart illustrating a flow example of an image analysis process according to the first embodiment.

FIG. 4 is a flowchart illustrating a flow example of the image analysis process according to the first embodiment. The flowchart process is started, for instance, when the user 9 performs the operation of instructing the start of the image analysis process.

First, the acquiring function 151 acquires the medical image as the analysis object from the medical image storage apparatus 201 (S1).

The collecting function 152 specifies non-image information related to the medical image acquired at S1 out of a plurality of pieces of non-image information regarding the patient. The collecting function 152 collects the specified non-image information as the collection object from the electronic medical chart system 202 (S2). For example, the non-image information as the collection object is set in advance as the information used for analysis out of the information regarding the patient as an imaging object of the medical image acquired at S1. The inputting function 153 inputs the collected non-image information to the analyzing function 154.

Subsequently, the analyzing function 154 analyzes the medical image acquired at S1 by using the non-image information acquired at S2 (S3). The analyzing function 154 transmits the analysis result to the display control function 155.

The display control function 155 causes the display 140 to display the analysis result of the medical image obtained by the analyzing function 154 (S4).

The collecting function 152 then determines whether the non-image information as the collection object is added to or updated in the electronic medical chart system 202 (S5).

When the non-image information as the collection object is added to or updated in the electronic medical chart system 202 ("Yes" at S5) and the updated non-image information satisfies the prescribed condition ("Yes" at S6), the collecting function 152 collects this non-image information (S7). When the non-image information is newly added, the collecting function 152 may collect the new non-image information without using the prescribed condition.

The analyzing function 154 reanalyzes the medical image acquired at S1 by using the additionally collected non-image information (S8).

The display control function 155 determines whether the analysis result differs before and after the reanalysis (S9). Note that the process at S9 may be executed by the analyzing function 154.

When determining that the analysis result differs before and after the reanalysis ("Yes" at S9), the display control function 155 notifies that the analysis result is updated (S10). For example, the display control function 155 causes the display 140 to display the message Ml as described using FIG. 3.

The receiving function 156 determines whether an operation of instructing display of the analysis result is received from the user 9 (S11). The display control function 155 continues to display the message Ml until the receiving function 156 receives the operation of instructing display of the analysis result from the user 9 ("No" at S11). The display of the message Ml may be terminated by an operation other than the operation of instructing display of the analysis result by use of an unillustrated closing button or the like.

When the receiving function 156 receives the operation of instructing display of the analysis result from the user 9 ("Yes" at S11), the display control function 155 displays the updated analysis result (S12).

Subsequently, the collecting function 152 determines whether the prescribed period has ended (S13). When the prescribed period has not ended ("No" at S13), the collecting function 152 determines whether the determination timing has come (S14). For example, the collecting function 152 determines that the determination timing has come ("Yes" at S14) when the prescribed time interval has elapsed since previous determination on whether the non-image information is updated in or added to the electronic medical chart system 202, or previous execution of the collection process of the non-image information. The process returns to S5 when the collecting function 152 determines that the determination timing has come.

When determining that the determination timing has not come yet ("No" at S14), the collecting function 152 stands by and repeats the process at S14.

When the collecting function 152 determines that the non-image information as the collection object is not added to nor updated in the electronic medical chart system 202 ("No" at S5), the collecting function 152 determines that the updated non-image information does not satisfy the prescribed condition ("No" at S6), or the display control function 155 determines that the analysis result does not differ before and after the reanalysis ("No" at S9), the process proceeds to S13.

When the collecting function 152 determines that the prescribed period has ended in the process at S13 ("Yes" at S13), the flowchart process is completed.

As described above, the analysis support apparatus 100a of the present embodiment automatically specifies the non-image information related to the medical image, and outputs the analysis result of the medical image using the specified non-image information. Thus, the analysis support apparatus 100a of the present embodiment can reduce the workload of the user 9 involved in the collection of the non-image information related to the medical image as the analysis object as compared to a case in which the user 9 manually collects and inputs various types of non-image information into the analysis application 40.

The analysis support apparatus 100a of the present embodiment specifies the non-image information used for analyzing the medical image by the analysis application 40, collects the specified non-image information, and analyzes the medical image based on the collected non-image information. The analysis support apparatus 100a of the present embodiment can thereby reduce the load of the user for collecting the non-image information required to analyze the medical image. The analysis support apparatus 100a of the present embodiment can also improve the analysis accuracy since the occurrence of input omission of the non-image information by the user 9 is reduced.

In the present embodiment, the non-image information used for analyzing the medical image is set in advance. The analysis support apparatus 100a of the present embodiment collects the information corresponding to the non-image information previously set to be used for analyzing the medical image out of the pieces of information stored in the electronic medical chart system 202. Thus, the analysis support apparatus 100a of the present embodiment reduces the workload of the user 9 for retrieving the non-image information used for analyzing the medical image from the pieces of information stored in the electronic medical chart system 202. In some cases, the non-image information dispersedly exists in various medical systems. In such a case, the analysis support apparatus 100a of the present embodiment reduces the workload of the user 9 by automatically collecting the non-image information used for analyzing the medical image.

Moreover, the user 9 may not notice that the non-image information is added or updated after generation of the initial analysis result. Even if the user 9 notices that the non-image information is added or updated by an alert function or the like of the electronic medical chart system 202, it is sometimes difficult for the user 9 to judge whether the added or updated non-image information influences the analysis of the medical image. Thus, the user 9 can overlook the addition or update of the non-image information that influences the analysis of the medical image, or incorrectly judge that the analysis of the medical image is not influenced.

In contrast, the analysis support apparatus 100a of the present embodiment determines whether the new non-image information as the collection object is stored in the electronic medical chart system 202 during the prescribed period after the initial collection, and collects the new non-image information as the collection object when the new non-image information as the collection object is stored in the electronic medical chart system 202. The analysis support apparatus 100a of the present embodiment makes it unnecessary for the user 9 to manually update or add the information in the electronic medical chart system 202 or the like, and automatically collects the added or updated information. The analysis support apparatus 100a of the present embodiment can thereby reduce the workload of the user 9 and reduce the occurrence of a problem in which the useful non-image information is not used for the analysis due to the oversight or misjudgment by the user 9.

The analysis support apparatus 100a of the present embodiment analyzes the medical image based on the collected non-image information. When the new non-image information is collected after the analysis of the medical image, the analysis support apparatus 100a of the present embodiment reanalyzes the medical image based on the new non-image information. Consequently, the analysis support apparatus 100a of the present embodiment can provide the analysis result reflecting the added non-image information to the user 9 even when the non-image information used for the analysis is added later.

The analysis support apparatus 100a of the present embodiment determines whether the collected non-image information is changed in the electronic medical chart system 202 during the prescribed period after the initial collection, and collects the changed non-image information when the non-image information is changed. Thus, the analysis support apparatus 100a of the present embodiment can reduce the occurrence of collection omission of the changed non-image information when the non-image information used for the analysis is changed after the analysis.

The analysis support apparatus 100a of the present embodiment collects the changed non-image information when the changed non-image information satisfies the prescribed condition. The analysis support apparatus 100a of the present embodiment can thereby reduce the repetition of recollection of the non-image information more than is necessary.

For example, the prescribed condition in the present embodiment is the threshold for the magnitude of the difference in the non-image information before and after the change. When the difference in the non-image information before and after the change is equal to or larger than the threshold, the analysis support apparatus 100a of the present embodiment collects the changed non-image information. Since the non-image information changed a little and having a low possibility of influencing the analysis result is excluded from the recollection object, the analysis support apparatus 100a of the present embodiment can reduce an increase in processing load while maintaining the accuracy of the analysis result.

The analysis support apparatus 100a of the present embodiment reanalyzes the medical image based on the changed non-image information when the changed non-image information is collected after the analysis of the medical image. Consequently, the analysis support apparatus 100a of the present embodiment can provide the analysis result reflecting the changed non-image information to the user 9 when the non-image information used for the analysis is changed after the analysis.

The analysis support apparatus 100a of the present embodiment notifies the user 9 that the analysis result of the medical image is updated when the medical image is reanalyzed and the analysis result differs before and after the reanalysis. Thus, the analysis support apparatus 100a of the present embodiment can encourage the user 9 to refer to the analysis result based on the latest non-image information. This assists the user 9 in reading the medical image based on the latest analysis result.

The analysis support apparatus 100a of the present embodiment changes the frequency of collection of the non-image information when the prescribed medical event occurs. Consequently, the analysis support apparatus 100a of the present embodiment can collect the non-image information at an appropriate timing according to a medical situation of the patient.

While the analysis of the CT image of the brain is employed as an example of the analysis of the medical image in the above description, the analysis support apparatus 100a of the present embodiment can be applied to a case other than this example. Hereinafter, a specific example of using the analysis support apparatus 100a of the present embodiment will be described.

In one example, the analyzing function 154 may be able to execute extracellular volume fraction (ECV) analysis of the heart. In the ECV analysis, the analyzing function 154 can improve the analysis accuracy by using the hematocrit of the patient obtained by a blood test for the image analysis. The hematocrit is an example of the non-image information.

For example, when the hematocrit of the patient is unknown at the time of the initial analysis, the analyzing function 154 analyzes the medical image of the patient without using the hematocrit. When the hematocrit of the patient is registered in the electronic medical chart system 202 during the prescribed period, the collecting function 152 collects the hematocrit. In this case, the analyzing function 154 updates the analysis result of the medical image by using the collected hematocrit. When the hematocrit of the patient registered in the electronic medical chart system 202 is changed, the collecting function 152 also collects the changed hematocrit. In this case, the analyzing function 154 updates the analysis result of the medical image by using the changed hematocrit.

Even when there is no information about the hematocrit, the ECV analysis can be performed. However, the analyzing function 154 can improve the analysis accuracy by using the hematocrit. The analyzing function 154 automatically reanalyzes the medical image based on the updated data when the blood test result of the patient is updated. This assists the user 9 in making a diagnosis based on the latest information.

In another example, the analyzing function 154 may be able to execute coronary artery plaque analysis. The coronary artery plaque analysis is typically important in diagnosing or predicting coronary artery disease. The analyzing function 154 can execute the coronary artery plaque analysis by analyzing a CT image or the like.

Since the blood test result of the patient, particularly, a low density lipoprotein (LDL) cholesterol level is information related to the growth of coronary artery plaque, the LDL cholesterol level is an object to be monitored by a doctor or the like. For example, the analyzing function 154 can improve the analysis accuracy by using the LDL cholesterol level for the analysis. The LDL cholesterol level is an example of the non-image information.

More specifically, the collecting function 152 monitors the LDL cholesterol level of the patient registered in the electronic medical chart system 202, and collects the LDL cholesterol level when the LDL cholesterol level exceeds a threshold. Alternatively, the collecting function 152 may collect the LDL cholesterol level of the patient when a change rate of the LDL cholesterol level satisfies a condition. The case in which the change rate satisfies the condition means, for example, that an increase rate from the LDL cholesterol level at a previous determination timing to the LDL cholesterol level at a present determination timing exceeds a threshold.

When the collecting function 152 collects the LDL cholesterol level, the analyzing function 154 executes the coronary artery plaque analysis again based on the latest information. The display control function 155 may cause the display 140 to display an alert when the LDL cholesterol level exceeds the threshold or when the change rate of the LDL cholesterol level satisfies the condition. For a disease such as coronary artery plaque where long term follow-up of the patient is conducted by a medical institution, the prescribed period during which the collecting function 152 collects the non-image information from the electronic medical chart system 202 may be continued over a long period of time. For example, the prescribed period may be continued while the patient continues to attend a hospital.

In still another example, the analysis support apparatus 100a may be used for monitoring cancer metastasis. For example, a whole-body CT image of a patient who has been treated for cancer is regularly captured during a follow-up period of the patient in some cases. The analyzing function 154 may analyze such a whole-body CT image.

Typically, even when the whole-body CT image is captured, a part to be focused on in the analysis is limited. For instance, in a whole-body CT image of a patient who was diagnosed with primary lung cancer and has been treated or is being treated, the lung is to be mainly analyzed. The analyzing function 154 may use various tumor marker values of the patient, as the non-image information, for analyzing the whole-body CT image. For example, when a tumor marker value of an organ other than the lung rises, the analyzing function 154 may intensively analyze the organ whose tumor marker value rises in addition to the lung.

The display control function 155 may also output the possibility of cancer metastasis to the organ whose tumor marker value rises as an alert. For example, when a-fetoprotein (AFP) as a tumor marker of liver cancer rises, the analyzing function 154 may execute an analysis process on a lesion part for liver cancer in addition to lung cancer. The display control function 155 may cause the display 140 to also display an alert indicating the possibility of metastasis to the liver. Additionally, when a part where primary cancer occurs and a part where the cancer metastasizes are treated in different departments, the display control function 155 may alert a doctor who belongs to the department for treating the part where the cancer metastasizes. The use of the change in the non-image information for the image analysis as described above enables the doctor to grasp a change in disease condition of the patient.

In the present embodiment, the analysis result of the medical image using the non-image information means the one obtained by using the non-image information during the analysis process of the medical image. However, the analysis result of the medical image using the non-image information may be the one obtained by applying processing or filtering based on the non-image information to the result of analyzing the medical image without using the non-image information as described above. The filtering means narrowing of an output object. For instance, the analyzing function 154 may narrow output information based on the non-image information out of information obtained by analyzing the medical image.

Second Embodiment

In the above first embodiment, the analysis support apparatus 100a includes the functions of the analysis application 40. In a second embodiment, a configuration in which the functions of the analysis application 40 are provided in an analysis apparatus different from the analysis support apparatus will be described.

Figure 5:
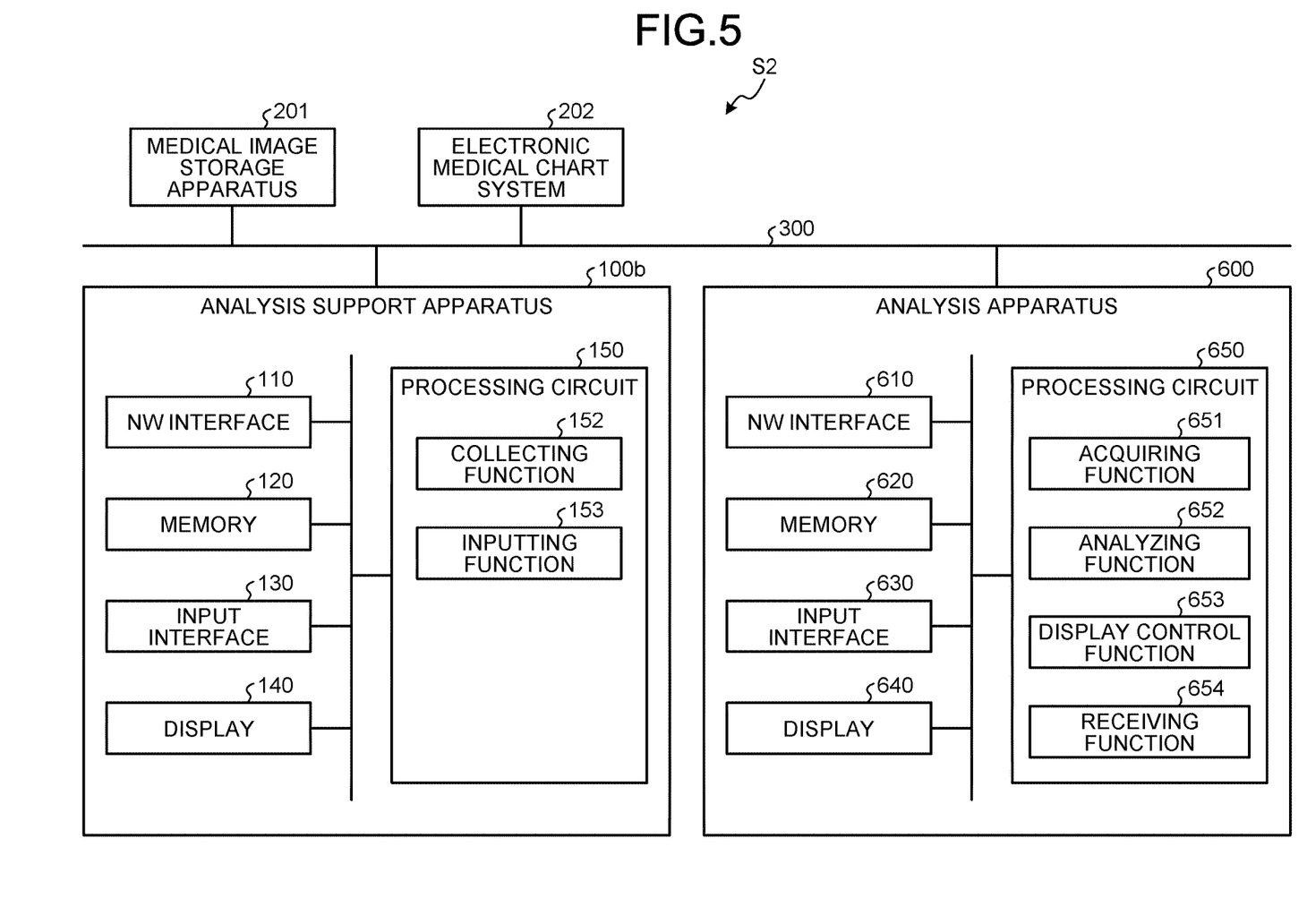
FIG. 5 is a diagram illustrating a configuration example of an analysis support system according to a second embodiment.

FIG. 5 is a diagram illustrating a configuration example of an analysis support system S2 according to the second embodiment. As illustrated in FIG. 5, the analysis support system S2 includes an analysis support apparatus 100b and an analysis apparatus 600. In the present embodiment, the analysis support system S2 does not include the medical image storage apparatus 201 and the electronic medical chart system 202. The analysis support system S2 may also include the medical image storage apparatus 201 and the electronic medical chart system 202. The analysis support apparatus 100b and the analysis apparatus 600 are connected to the medical image storage apparatus 201 and the electronic medical chart system 202 via the network 300 so as to allow communication therebetween.

The analysis support apparatus 100b includes the NW interface 110, the memory 120, the input interface 130, the display 140, and the processing circuit 150 similarly to the first embodiment.

The analysis apparatus 600 includes a network (NW) interface 610, a memory 620, an input interface 630, a display 640, and a processing circuit 650. The display 640 is an example of the display unit in the present embodiment.

The processing circuit 150 of the analysis support apparatus 100b includes the collecting function 152 and the inputting function 153. The collecting function 152 is an example of the collecting unit. The inputting function 153 is an example of the inputting unit.

The processing circuit 650 of the analysis apparatus 600 includes an acquiring function 651, an analyzing function 652, a display control function 653, and a receiving function 654. The acquiring function 651 is an example of the acquiring unit. The analyzing function 652 is an example of the analyzing unit. The display control function 653 is an example of the display control unit. The analysis apparatus 600 may be an example of the analyzing unit.

The collecting function 152 of the analysis support apparatus 100b has a function similar to that of the first embodiment. More specifically, the collecting function 152 collects the non-image information used for analyzing the medical image by the analysis apparatus 600 from one or a plurality of medical information processing apparatuses, e.g., the electronic medical chart system 202.

The inputting function 153 of the analysis support apparatus 100b inputs the non-image information collected by the collecting function 152 to the analysis apparatus 600.

The acquiring function 651 of the analysis apparatus 600 has a function similar to the acquiring function 151 of the analysis support apparatus 100a of the first embodiment.

The analyzing function 652 of the analysis apparatus 600 has a function equivalent to the analysis application 40 described using FIG. 1. That is, the analyzing function 652 has a function similar to the analyzing function 154 of the analysis support apparatus 100a of the first embodiment. More specifically, the analyzing function 652 analyzes the medical image regarding the patient by using the non-image information regarding the patient collected by the analysis support apparatus 100b.

The display control function 653 of the analysis apparatus 600 has a function similar to the display control function 155 of the analysis support apparatus 100a of the first embodiment.

The receiving function 654 of the analysis apparatus 600 has a function similar to the receiving function 156 of the analysis support apparatus 100a of the first embodiment.

Even in the configuration in which the analysis apparatus 600 and the analysis support apparatus 100b are separated as described above, such an effect as to reduce the workload of the user 9 involved in the collection of the non-image information used for analyzing the medical image can be obtained similarly to the first embodiment.

Modification

In the above respective embodiments, the collecting function 152 collects the non-image information only when the non-image information is updated and this non-image information satisfies the prescribed condition. However, a configuration in which the prescribed condition is not imposed may be employed. That is, the collecting function 152 may collect the changed non-image information regardless of the changed contents when the non-image information is changed.

Additionally, in the above respective embodiments, the prescribed condition is used for determining whether the collecting function 152 collects the non-image information. However, the prescribed condition may be used for determining whether the analyzing function 154 executes reanalysis. For example, suppose that the collecting function 152 collects the changed non-image information regardless of the changed contents. In this case, the analyzing function 154 may execute reanalysis by using the non-image information only when the non-image information satisfying the prescribed condition is collected.

Moreover, the functions of the analysis support apparatuses 100a, 100b or the analysis apparatus 600 described in the above respective embodiments may be partially or wholly executed in a cloud environment.

Various data treated in the present specification are typically digital data.

In accordance with at least one of the embodiments described above, the workload of the user 9 involved in the collection of the non-image information related to the medical image as the analysis object can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analysis support apparatus comprising
processing circuitry configured to:
acquire a medical image that a patient is imaged;
collect one or more pieces of non-image information predefined to be used for analysis of the medical image out of a plurality of pieces of non-image information regarding the patient;
analyze the medical image based on the collected non-image information; and
display an analysis result of the medical image on a display, wherein
the processing circuitry is further configured to change a frequency of collection of the non-image information when a prescribed medical event occurs, and
the prescribed medical event includes at least one of a definite diagnosis of the patient made, a determination of medical service fees for diagnosing the patient, or a completion of a post-diagnostic follow-up period for the patient.

2. The analysis support apparatus according to claim 1, wherein
the non-image information related to the medical image is non-image information required to analyze the medical image.

3. The analysis support apparatus according to claim 1, wherein
the non-image information used for analyzing the medical image is set in advance, and
the processing circuitry is configured to specify, as non-image information required to analyze the medical image, information corresponding to the non-image information previously set to be used for analyzing the medical image out of a plurality of pieces of information stored in one or a plurality of medical information processing apparatuses, and
collect the specified non-image information.

4. The analysis support apparatus according to claim 1, wherein
the processing circuitry is configured to determine whether new non-image information regarding the patient is stored in one or a plurality of medical information processing apparatuses during a prescribed period after initial collection, and
collect the new non-image information when the new non-image information is stored in the one or plurality of medical information processing apparatuses.

5. The analysis support apparatus according to claim 4, wherein
the processing circuitry is configured to
analyze the medical image based on the collected non-image information, and
reanalyze the medical image based on the new non-image information when the new non-image information is collected after the analysis of the medical image.

6. The analysis support apparatus according to claim 1, wherein
the processing circuitry is configured to
determine whether the collected non-image information is changed in one or a plurality of medical information processing apparatuses during a prescribed period after initial collection, and
collect the changed non-image information when the non-image information is changed.

7. The analysis support apparatus according to claim 6, wherein
the processing circuitry is configured to
analyze the medical image based on the collected non-image information, and
reanalyze the medical image based on the changed non-image information when the changed non-image information is collected after the analysis of the medical image.

8. The analysis support apparatus according to claim 1, wherein
the processing circuitry is configured to
determine whether the collected non-image information is changed in one or a plurality of medical information processing apparatuses during a prescribed period after initial collection, and
collect the changed non-image information when the non-image information is changed and the changed non-image information satisfies a prescribed condition.

9. The analysis support apparatus according to claim 8, wherein
the prescribed condition is a threshold for magnitude of a difference in the non-image information before and after the change, and
the processing circuitry is configured to collect the changed non-image information when the difference in the non-image information before and after the change is equal to or larger than the threshold.

10. The analysis support apparatus according to claim 1, wherein
the processing circuitry is configured to notify a user that the analysis result of the medical image is updated when the medical image is reanalyzed and the analysis result differs before and after the reanalysis.

11. The analysis support apparatus according to claim 1, wherein
the processing circuitry is configured to analyze the medical image based on the collected non-image information by executing an analysis application for analyzing the medical image.

12. The analysis support apparatus according to claim 1, wherein the processing circuitry is configured to
display an interactive message indicating an explanation of updated non-image information, and
display the updated non-image information upon activation by a user.

13. An analysis support system comprising an analysis apparatus and an analysis support apparatus,
the analysis apparatus including a first processing circuitry configured to analyze a medical image regarding a patient by using non-image information regarding the patient, and
the analysis support apparatus including a second processing circuitry configured to collect the non-image information predefined for analyzing the medical image by the analysis apparatus from one or a plurality of medical information processing apparatuses,
display an analysis result of the medical image on a display, and
input the collected non-image information into the analysis apparatus, wherein
the processing circuitry is further configured to change a frequency of collection of the non-image information when a prescribed medical event occurs, and the prescribed medical event includes at least one of a definite diagnosis of the patient made, a determination of medical service fees for diagnosing the patient, or a completion of a post-diagnostic follow-up period for the patient.

14. An analysis support method comprising:

acquiring a medical image that a patient is imaged;

collecting one or more pieces of non-image information predefined to be used for analysis of the medical image out of a plurality of pieces of non-image information regarding the patient;

analyzing the medical image based on the collected non-image information;

displaying an analysis result of the medical image on a display; and changing a frequency of collection of the non-image information when a prescribed medical event occurs;

wherein the prescribed medical event includes at least one of a definite diagnosis of the patient made, a determination of medical service fees for diagnosing the patient, or a completion of a post-diagnostic follow-up period for the patient.

* * * * *